(12) United States Patent
Turovets

(10) Patent No.: US 10,066,936 B2
(45) Date of Patent: Sep. 4, 2018

(54) TEST STRUCTURES AND METROLOGY TECHNIQUE UTILIZING THE TEST STRUCTURES FOR MEASURING IN PATTERNED STRUCTURES

(71) Applicant: NOVA MEASURING INSTRUMENTS LTD., Rehovot (IL)

(72) Inventor: Igor Turovets, Moshav Givat Yarim (IL)

(73) Assignee: NOVA MEASURING INSTRUMENTS LTD, Rehovot (IL)

( * ) Notice: Subject to any disclaimer, the term of this patent is extended or adjusted under 35 U.S.C. 154(b) by 16 days.

(21) Appl. No.: 15/124,445

(22) PCT Filed: Mar. 10, 2015

(86) PCT No.: PCT/IL2015/050253
§ 371 (c)(1),
(2) Date: Sep. 8, 2016

(87) PCT Pub. No.: WO2015/136533
PCT Pub. Date: Sep. 17, 2015

(65) Prior Publication Data
US 2017/0023357 A1    Jan. 26, 2017

Related U.S. Application Data

(60) Provisional application No. 61/950,248, filed on Mar. 10, 2014.

(51) Int. Cl.
*G01B 11/02* (2006.01)
*G01B 11/27* (2006.01)
(Continued)

(52) U.S. Cl.
CPC .......... *G01B 11/272* (2013.01); *G01N 21/47* (2013.01); *G01N 21/4788* (2013.01);
(Continued)

(58) Field of Classification Search
CPC .. G01B 11/272; G01N 21/47; G01N 21/4788; G01N 21/9501; G01N 21/95607
See application file for complete search history.

(56) References Cited

U.S. PATENT DOCUMENTS 8,283,111 B2    10/2012  Fonseca et al.
2005/0122516 A1*  6/2005  Sezginer ............. G03F 7/70633
                                                        356/401
(Continued)

*Primary Examiner* — Kimberly Rizkallah
*Assistant Examiner* — Maria Ligai
(74) *Attorney, Agent, or Firm* — Browdy and Neimark, PLLC

(57) ABSTRACT

An article is presented configured for controlling a multiple patterning process, such as a spacer self-aligned multiple patterning, to produce a target pattern. The article comprises a test site carrying a test structure comprising at least one pair of gratings, wherein first and second gratings of the pair are in the form of first and second patterns of alternating features and spaces and differ from the target pattern by respectively different first and second values which are selected to provide together a total difference such that a differential optical response from the test structure is indicative of a pitch walking effect.

22 Claims, 7 Drawing Sheets

(51) Int. Cl.
*H01L 21/66* (2006.01)
*G01N 21/47* (2006.01)
*G01N 21/956* (2006.01)
*G01N 21/95* (2006.01)
*H01L 21/033* (2006.01)

(52) U.S. Cl.
CPC ... *G01N 21/9501* (2013.01); *G01N 21/95607* (2013.01); *H01L 21/0337* (2013.01); *H01L 22/30* (2013.01); *G01B 2210/56* (2013.01); *G01N 2021/95615* (2013.01); *G01N 2201/12753* (2013.01)

(56) References Cited

U.S. PATENT DOCUMENTS

| | | | |
|---|---|---|---|
| 2007/0061773 A1 | 3/2007 | Ye et al. | |
| 2008/0174778 A1* | 7/2008 | Ke | G03F 7/70625 356/400 |
| 2014/0036243 A1* | 2/2014 | Beyer | G03F 1/72 355/52 |

* cited by examiner (GENERAL ART)

(GENERAL ART)

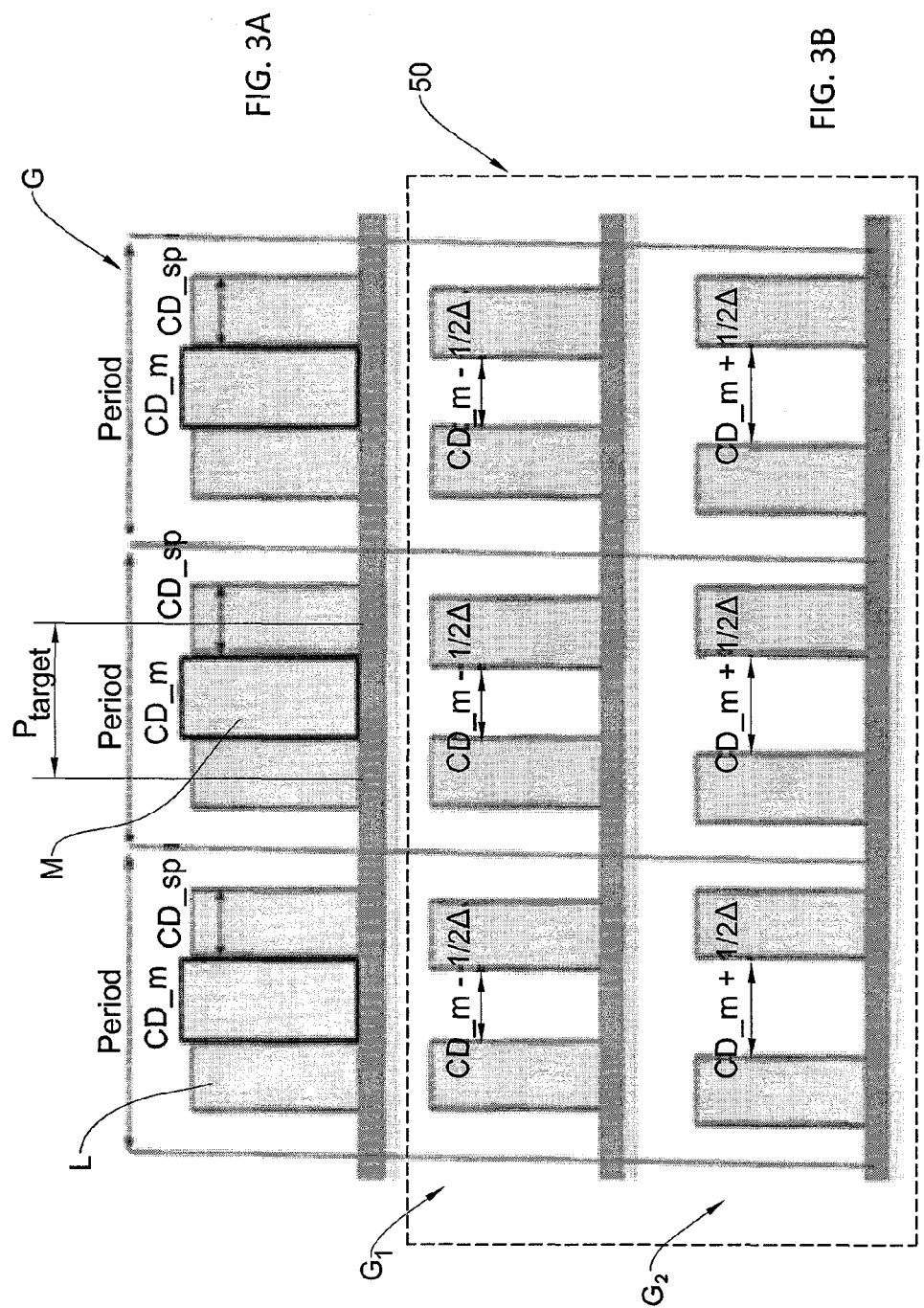

TEST STRUCTURES AND METROLOGY TECHNIQUE UTILIZING THE TEST STRUCTURES FOR MEASURING IN PATTERNED STRUCTURES

TECHNOLOGICAL FIELD

The present invention is generally in the field of metrology techniques, and relates to a metrology method and system for measuring in patterned samples utilizing test structures.

BACKGROUND

Metrology processes are used for monitoring and controlling various steps of a semiconductor manufacturing process by measuring parameters of a wafer, such as line width, thickness, angle, etc. As a demand for shrinking semiconductor devices continues to increase, multiple patterning technologies are used for manufacturing integrated circuits (ICs) to enhance the pattern feature density.

A simplest example of the multiple patterning techniques is a double patterning, which allows the patterning of smaller features at a smaller pitch than what is currently possible with standard lithographic techniques. To this end, standard lithographic pattern-and-etch techniques can be applied to the same substrate twice, thereby forming larger patterns spaced closely together to achieve a smaller feature size than would be possible by single exposure. During double patterning, a layer of radiation-sensitive material on the substrate is exposed to a first pattern, which is developed and transferred to an underlying layer using an etching process, and then these standard lithography steps are repeated for a second pattern, while shifting the second pattern relative to the first pattern.

Another approach to double the resolution of a lithographic pattern is to utilize a dual-tone development technique, wherein a layer of radiation-sensitive material on the substrate is exposed to a pattern of radiation, and then a double pattern is developed into the layer of radiation-sensitive material. Such dual-tone development techniques are described for example in U.S. Pat. No. 8,283,111.

In general, multiple patterning lithography process, which may be double, triple, quadruple, etc. patterning process, requires multiple photolithographic masks for the printing of a single layer on a wafer. Therefore, a multiple patterning lithography process adds a new contribution to the overlay error, which is associated with a placement error of two or several masks used to form the pattern for a single layer on the wafer. An overlay error in a pattern generated with a self-aligned double patterning technique is known as "pitch walking" effect.

For example, US patent publication No. 2014/036243 describes a method for correcting at least one error on wafers processed by at least one at least two photolithographic masks used in a multiple patterning lithography process. This method includes measuring the at least one error at a wafer processing site, and modifying the at least one photolithographic mask by introducing at least one arrangement of local persistent modifications in the photolithographic mask. This technique suggests using a so-called hard material photo resist of a sacrificial layer on top of a layer to be etched in a self-aligned double patterning process, and introducing an arrangement of local persistent modifications or the pixels in the sacrificial layer to avoid a variation of the lines during the etching of said layer underneath the sacrificial layer, to thereby prevent "pitch walking" effects during the etching step.

GENERAL DESCRIPTION

As described above, multiple patterning applications, such as spacer self-aligned multiple patterning (pitch splitting) create arrays of lines/spaces with overlay appearance as a difference between lines and spaces that are located at the same level (same material and same layer). Pitch splitting is done to overcome limitations of the illumination wavelength and numerical apertures used at the exposure stage.

Usually, measurements of the multiple patterning applications are performed on real structures, with real design rules periods/CDs. This makes the "standard" overlay (OL) measurement techniques less applicable for monitoring and controlling the multiple patterning processes. Both Image Based Overlay (IBO) and Diffraction Based Overlay (DBO) have difficulties for measuring structures with minimal periods and CDs and may require larger features. For majority of multiple patterning schemes, especially for such applications as Spacer Self-Aligned Double Patterning (SADP), it is difficult to create features that are much larger than design rules. In addition, modern and promising overlay measurement techniques, such as first order DBO and Muller Matrix based DBO schemes, while being considered as capable of perfectly measuring regular overlay, cannot show benefits in measurements of such an effect as "pitch walking" due to the lack of asymmetry. As indicated above, the pitch walking effect is associated with an overlay error in a pattern generated with a self-aligned multiple patterning technique.

The present invention provides a novel design and optimization of a test site for controlling a multiple patterning process. It should be noted that for the purposes of the present application, the term "test site" used herein refers to a site on a patterned article, while the patterned article may be constituted by a sample (e.g. semiconductor wafer) to be patterned by multiple patterning process, and is present on the patterning mask(s) used in the multiple patterning process.

Also, the invention provides a data processing technique utilizing special algorithms and interpretation sequence (model based approach) to allow fast and accurate interpretation of pitch walking (together with all other required parameters), and/or special data processing to allow modeless measurements of pitch walking based on calibration.

It should also be noted that the technique of the present invention does not require modification of existing scatterometry measurement systems and various measurement hardware can be utilized. Raw measurement data for "pitch walking" can be obtained by using oblique or normal-incidence reflectometry, ellipsometry, angle-resolved and phase-based systems or combinations thereof. Broadband or predetermined wavelength(s), various polarizations, various angles of incidence and azimuth could be used. Bright, dark and "grey-field" configurations also could be used.

According to one broad aspect of the invention, there is provided an article comprising a test site carrying a test structure configured for controlling a multiple patterning process to produce a target pattern, the test structure comprising at least one pair of gratings, wherein first and second gratings of the pair are in the form of first and second patterns of alternating features and spaces and differ from the target pattern by different first and second values which are selected to provide together a total difference such that a differential optical response from said test structure is indicative of the pitch walking effect.

The differential optical response from said test structure indicative of the pitch walking effect is measured as a function of at least one varying measuring condition, e.g. wavelength, polarization, angle.

The first and second differences from the target pattern are selected such that if there is no pitch walking effect (overlay error) or pitch walking effect below the predefined limit, the differential optical response would actually be zero, or generally be less than a predetermined threshold. Only in case there is pitch walking effect induced by the patterning, the differential optical response is within the detectable range.

According to another broad aspect of the invention, there is provided an article comprising a test site carrying a test structure configured for controlling a multiple patterning process to produce a target pattern, the test structure comprising at least one pair of gratings, first and second grating of the pair being arranged in first and second spaced-apart regions of the test site, each grating presenting a pattern formed by an array of alternating features and spaces, wherein said first and second gratings of the pair are configured such that they have first and second values for at least one pattern parameter which are different from a corresponding parameter of the target pattern by predetermined difference value selected such that a total difference of the pattern parameter for said at least one pair of gratings from the corresponding pattern parameter of the target pattern corresponds to a pitch walking effect expected in the multiple patterning process which is to be controlled.

The article carrying the test site may be a sample to undergo the multiple patterning process, or may be a mask (e.g. mandrel) for use in the multiple patterning process.

The test structure may include more than one pair of gratings. The number of gratings in the test structure may or may not be equal to the number of patterning steps in the multiple patterning process (the number of the gratings in the test structure may be smaller than a number of patterning steps in the multiple patterning process).

The predetermined difference value may be selected to be proportional to a predefined value corresponding to the process window of the pitch walking effect.

In some embodiments, the at least one pattern parameter comprises a feature/space dimension of the pattern (width of line and/or space). The predetermined value by which the feature/space of the grating in the test structure is different from the feature/space dimension of the target pattern is selected to be proportional to a predefined value corresponding to the pitch walking effect characterizing the multiple patterning process to be controlled. The proportion factors for the different gratings are selected such that the total difference for the pair (or more) of gratings from the feature/space dimension of the target pattern is substantially equal to the predefined value corresponding to the pitch walking effect.

In some embodiments, the first and second patterns of the pair of gratings in the test structure are configured for controlling double patterning process. In these embodiments, considering the two test gratings (pair), the first and second patterns having the first and second feature/space dimensions $(CD\_m)_1$ and $(CD\_m)_2$ are selected to satisfy a condition:

$$(CD\_m)_1 = CD\_m + (0.5\Delta) \text{ and } (CD\_m)_2 = CD\_m - (0.5\Delta),$$

wherein $CD\_m$ is the feature/space dimension in the target pattern; and $\Delta$ is the predefined value corresponding to the process window of the pitch walking effect characterizing the double patterning process.

As indicated above, in some embodiments, the article with the test structure may be a real sample (e.g. wafer) prepared to undergo the multiple patterning process to be controlled. Also, such article may be a patterning mask for use (e.g. as a mandrel mask) in the multiple patterning process to be applied to a sample.

It should be noted that although the pattern parameter of the test grating modified with respect to that of the target pattern is referred to herein below as "feature", the same is applicable for "space" parameter.

According to yet another aspect of the invention, there is provided a method for use in controlling a multiple patterning process applied to a sample to produce a target pattern thereon. The method comprises: providing the above-described test structure within a test site on the sample; applying optical measurements to the test structure and detecting optical responses of the gratings of the test structure; and processing and analyzing data indicative of the detected optical responses to determine a pitch walking effect characterizing the multiple patterning process being applied to the sample.

Preferably, the optical measurements comprise measurements with different measurement conditions, such that the optical responses are in the form of detected light as functions of said measurement condition. The different measurement conditions comprise at least one of the following: different wavelengths of illumination, different polarizations, different angles of light collection.

In some embodiments, the processing and analyzing of the data indicative of the optical response is based on a predetermined model. In this case, the processing and analyzing of the measured data may include: determining an average of the optical response function for the first and second gratings, and a difference of the optical response function between the first and second gratings; utilizing a predetermined model for interpreting the average function and the difference function for the predetermined difference value corresponding to the process window of pitch walking effect and obtaining data indicative of the pitch walking effect.

In some other embodiments, the processing and analyzing of the data indicative of the optical response functions is modeless and is based on predetermined calibration data. In this case, a difference of the optical response function between the first and second gratings is determined, and analyzed utilizing the calibration data, to thereby obtain data indicative of the pitch walking effect.

The article with the test structure can be provided by carrying out the following: applying a mandrel mask to an article to create a first, core pattern thereon, where the mandrel mask comprises a mandrel layout defining a test site carrying a test structure, thereby creating a corresponding test structure within a test site on the article, while forming the mandrel pattern thereon. The said test structure in the mandrel comprises at least first and second gratings having first and second patterns with respective first and second critical dimensions which are different from a critical dimension of the mandrel layout by predetermined first and second values selected in accordance with expected pitch walking effect characterizing the multiple patterning process.

It should be noted that although for simplicity the present invention is exemplified in the description below as relating to SADP application, the principles of the present invention are applicable for any other double-patterning and, generally, multiple-patterning schemes and applications.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 3A and 3B illustrate schematically the principles of the invention for designing a tests structure for controlling multiple patterning process, in a non-limiting example of a sample manufactured by a SADP-type multiple patterning process (FIG. 3A) and for a on limiting example of test structure including one pair of gratings (FIG. 3B);

FIG. 5A shows spectral sensitivity to pitch walking due Litho (Mandrel) error Y (left), and FIG. 5B shows Spectral sensitivity to pitch walking due to spacer error X; FIG. 6A shows the difference spectra for Mandrel error and FIG. 6B shows the difference spectra for spacer error.

DETAILED DESCRIPTION OF EMBODIMENTS

The present invention provides a novel design for a test structure to be used in multiple patterning process enabling monitoring and controlling this process by optical critical dimensions (OCD) measurements. The test structure is formed within a test site of a real sample, that can be located on a semiconductor wafer either within the scribe line or within an in-die region.

As indicated above, for simplicity, the invention is exemplified herein with reference to SADP process. Such process is known per se and therefore need not be described in details. Briefly, SADP process is a pitch-splitting sidewall image method that utilizes two masks: a core mask and a trim mask. The core mask, which is the first mask in the SADP process flow, defines core mandrel patterns (the printed pattern generated by the core mask), and the sidewall spacer is deposited onto all sides of a mandrel pattern to enable pitch doubling in the patterning. The trim mask removes unnecessary patterns by blocking or unblocking with photoresist (PR).

Generally, there are two types of SADP process used for the state-of-the-art lithography patterning: SIM-type SADP and SID-type SADP, which actually differ from one another in starting from negative or positive patterning step. SIM-type SADP refers to "spacer is metal" configuration, where the sidewall spacer itself becomes the final metal patterns. SID-type SADP refers to "spacer is dielectric" configuration. In the double-patterning process, a first patterning step is performed using a core (Mandrel) mask. This mask is designed based on the CDs of the final pattern to be obtained by the double-patterning. Accordingly, the mandrel layout/ pattern includes the features with the CD of the target pattern arranged with a period P which relates to a target pattern period $P_{target}$ as $$P=nP_{target},$$

where n is the number of patterning steps, and for double patterning the mandrel layout period P is twice the target period $P_{target}$.

Figure 1:
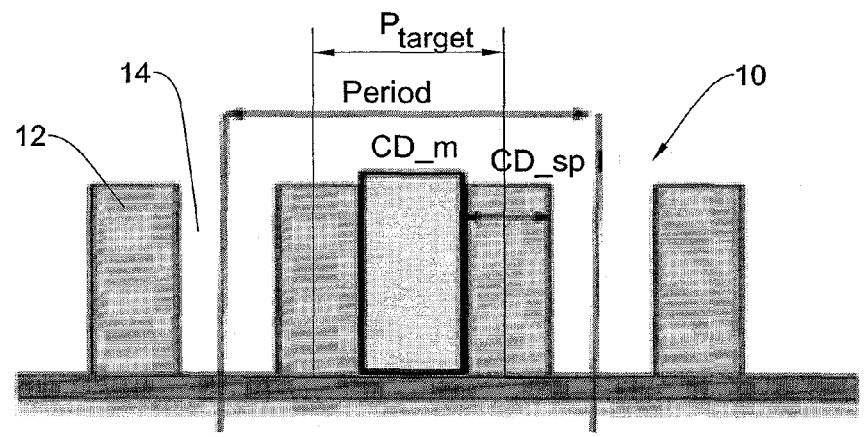
FIGS. 1 and 2 illustrate schematically the general principles of "pitch walking" effect resulting from multiple patterning process, exemplified for SADP application.

In this connection, reference is made to FIG. 1 illustrating schematically the principles of multiple patterning using a double-patterning example. The figure shows a pattern 10 of lines 12 and spaces 14 created with the above described SADP. As shown, the mandrel layout pattern is first created in the form of an array of spaced-part features (only one such feature being shown in the figure) having a width CD_m and arranged with Period being twice a period of the target pattern $P_{target}$. Then, a spacer material is deposited above the first pattern, followed by an anisotropic etching to create a spacer and mandrel removal to thereby produce a second pattern of spaced-apart spacer features having a width CD_sp.

Figure 2:
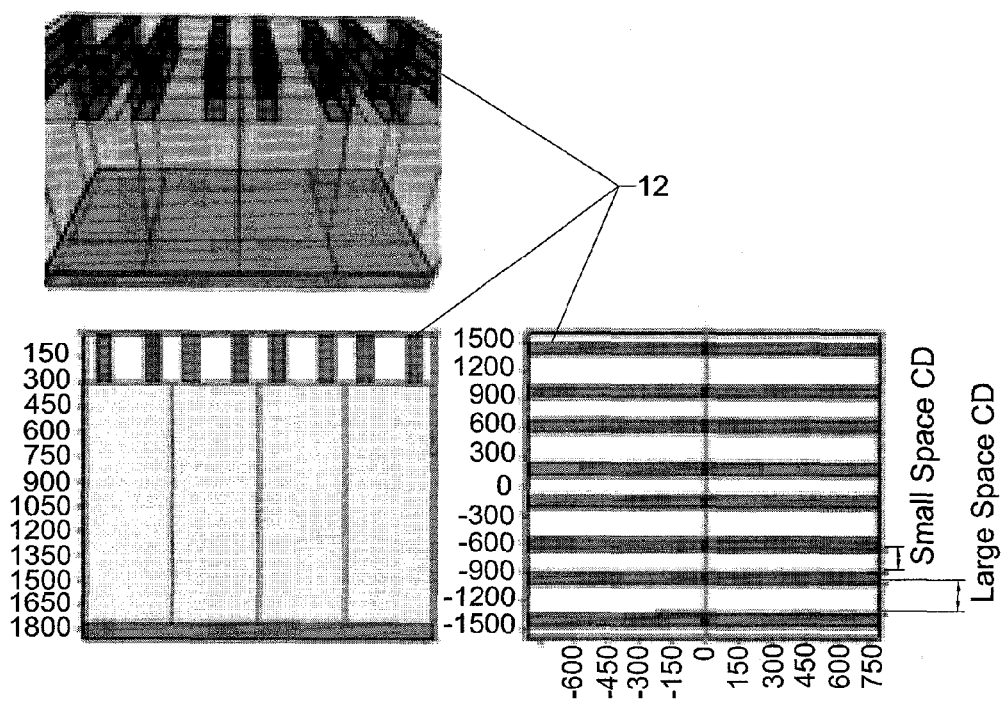

After such etch stage, all lines 12 have the same dimension (width) CD_sp defined by the CD of a spacer. Spaces 14 between lines 12 can be different: one of the spaces is defined by original litho (Mandrel) pattern CD_m, while the second space is induced being actually defined by deviations of both the litho pattern CD_m and the spacer CD_sp from the target values. This is illustrated in FIG. 2 showing lines 12 created by SADP, where all lines 12 have the same width, CD_sp, but spaces between the lines 12 are different defining Large Space CD and Small Space CD. A difference between them is defined by pitch walking effect. The pitch walking is practically induced by deviation of both the CD spacer and the Litho (Mandrel) from the target values.

Direct measurement of pitch walking (or differences between two adjustment spaces) is problematic for the standard Optical Critical Dimension (OCD) techniques that are less sensitive to the CD difference, especially when differences are small Pitch walking (or differences in CDs of two spaces) is usually small, and its effect on the optical response of the sample is weak, and it is thus difficult to measure pitch walking parameter compared to the CD of the line.

Moreover, even if Space CD difference, CD_sp, is measured, it is difficult to distinguish between the processes that contributed for the observed difference. In this example, there is a large difference between Large Space CD and Small Space CD. Even assuming that the difference between Large Space CD and Small Space CD is successfully measured by OCD, together with the line width CD_sp, OCD has difficulty to distinguish whether such difference between Large Space CD and Small Space CD is due to larger or smaller CD printed at Litho, i.e. whether Large CD was created by Litho (Litho underexposure created larger CD_m=Large CD), or Small CD was due to Litho (Litho overexposure created smaller CD_m=Small CD). In both cases, the same result can be obtained after double patterning, thus limiting usability of usage of measurement results for feedback and process control. This problem is becoming more acute and more difficult to solve for triple, quadro, etc. patterning, which is becoming more widespread, as required at the advanced technology nodes.

As described above, in the SADP application, Litho line (Mandrel) is printed with CD_m and Period that is twice larger than a target period $P_{target}$. Generally, for multiple patterning technique including n patterning steps (masks) the period P of the first mask (mandrel pattern) is $P=nP_{target}$. Then, during a sequence of the process steps, the mandrel pattern is covered by spacer (CD_sp). After processing and mandrel removal, two equal spacer lines are created in the original double period P. In the case that $$CD\_m = CD\_sp = \frac{1}{4} \cdot \text{Period},$$

in the final structure there will be two lines arranged with half of the original period P, or actually a grating with period P/2, which is $P_{target}$ of the final pattern.

For the general multiple patterning process of n patterning steps, the final target pattern is in the form of lines with the predefined width CD_m arranged with a period $P_{target}$=P/n (P being the nominal period of the mandrel pattern, i.e. first patterning mask).

In order to measure final result of real multiple patterning process (e.g. SADP), at least two CDs need to be measured, CD_sp, and CD_m. Current OCD techniques are barely capable to measure CD_sp and delta between the two spaces, Large Space CD and Small Space CD (shown in FIG. 2).

The present invention solves the above problem of directly monitoring/controlling the multiple patterning processes by providing a novel test structure configuration. Such a test structure is typically prepared/produced within a test site on a patterned article (e.g. in scribe lines or in-die region on a wafer, or on a patterning mask). The test structure includes a plurality of at least two patterns (gratings) located in at least two spaced-apart regions of the test site, respectively, each grating being in the form of spaced-apart features. These plurality of at least two gratings includes a pair of gratings/patterns, which have different widths (CDs) of the pattern features, (CD_m)₁ and (CD_m)₂ satisfying the following condition:

$$(CD\_m)_1 = CD\_m + (A \cdot \Delta) \text{ and } (CD\_m)_2 = CD\_m - (B \cdot \Delta)$$

where CD_m is the CD (width) of the feature (line) in the final pattern (target pattern) to be obtained as a result of the multiple patterning process, which is defined by the CD of the mandrel mask, and (A·Δ) and (B·Δ) describe the deviation from the nominal CD of the mandrel mask such that these two gratings of the test structure have respectively smaller CDs and larger CDs as compared to CDs of the final pattern, i.e. pattern defined by the Litho (Mandrel) CD, CD_m.

It should be noted that the value of Δ is selected to correspond to the expected process window of pitch walking effect resulting from a specific multiple patterning process which is to be controlled. As for the coefficients A, B they are selected in accordance with the number k of gratings of the test structure used in the process control (i.e. k is equal or less than the entire number of gratings in the test structure) such that the total difference between the deviations from the nominal CD of the mandrel mask induced by all k gratings provides the selected Δ value.

Thus, in the example of two gratings, i.e. k=2, (A·Δ)−(B·Δ)=Δ, A=0.5 and B=−0.5.

In this connection, it should be noted that a number of gratings in the test structure may or may not be equal to the number of patterning steps of the multiple patterning process to be controlled. For example, under certain conditions, double, triple and quadruple patterning can be properly controlled by a test structure including only one pair of such gratings The principles of the invention for the test structure configuration are exemplified in FIGS. 3A and 3B. FIG. 3A illustrates a standard grating (pattern) G resulting from a multiple patterning process, e.g. SADP similar to that of FIG. 1. The grating/pattern G includes an array of spaced apart features L arranged with a period $P_{target}$ and characterized by CD_m and CD_sp parameters as described above. FIG. 3B illustrates a test structure 50 configured according to the invention, for controlling the multiple patterning process used for creating pattern G by any suitable OCD technique. In the present not limiting example, the test structure 50 includes two different gratings $G_1$ and $G_2$ having $(CD\_m)_1$ and $(CD\_m)_2$ parameters satisfying the following condition:

$$(CD\_m)_1 = CD\_m - 0.5\Delta \quad (CD\_m)_2 = CD\_m + 0.5\Delta$$

where one grating $G_1$ has smaller CDs, and the other grating $G_2$ has larger CDs; in this specific example this differences from the CD_m (CD of the target pattern) being of the same value and opposite sign, to satisfy the condition described above.

These gratings $G_1$ and $G_2$ are properly designed and formed together within a test site in a patterning mask, so all geometrical parameters on printed profiles of both gratings $G_1$ and $G_2$ of the test structure 50 are similar, with the exception of the small difference in Litho CDs. Delta from the target CDs (Δ) is equal or slightly smaller than the window of the Litho process within all design rules.

After the SADP, in the ideal case, proposed pair of gratings will be exactly the same. As shown in FIG. 2, in both gratings there will be two different spaces: one space equal to (P/4−½Δ), and the other to (P/4+½Δ), where P is the nominal period of the mandrel (1ˢᵗ mask). Let us now consider a measurement signal from the test structure, corresponding to an optical response of the test structure. In this connection, it should be noted that optical measurements are preferably performed using varying measurement condition(s), such as wavelength, polarization, angle of light collection. Accordingly, the optical response is in the form of detected light as a function of the measurement condition. This may be a spectral response, or a so-called "pupil" or "angular" response (i.e. signal distribution in a pupil plane).

These pair of gratings in the ideal case will show the same measurement signal. However, things will change if there is a deviation due to the process, such as if CD_sp and/or CD_m deviate from the nominal ¼ of period, causing pitch walking. In this case, the optical responses from the two gratings will be different, and this difference will clearly show process deviations.

Table 1 provides explanation of the dimensions of the gratings of the test structure for pitch walking measurements and pitch walking components Δ, X and Y, where Δ is target difference in CDs of the spaces as described above, and X and Y correspond to respectively Spacer and Litho (Mandrel) pitch walking error components.

TABLE 1

|  | Mandrel Period | CD Mandrel (target) | Spacer (target) | Pitch walking (target) | Pitch walking due to CD Spacer (+x) | Pitch walking due to Litho (+Y) |
|---|---|---|---|---|---|---|
| Standard OCD Grating | P | ¼ P | ¼ P | zero | +2x | +2Y |
| Grating 1 | P | ¼ P + ½ Δ | ¼ P | Δ | Δ +2X | Δ +2Y |
| Grating 2 | P | ¼ P − ½ Δ | ¼ P | −Δ | −Δ +2X | −Δ +2Y |

Here, parameter (variable) X represents possible process deviations of Spacer CD, and Y represents process variations of the Mandrel CD, both variations create pitch walking; and Delta $\Delta$ is the difference between pair of gratings selected to correspond to the expected process window of pitch walking effect.

With the test structure of the invention, deviations of either one or both of CD_sp (X) and CD_m (Y) is embedded in pair of different gratings. This difference, translated also into spectral difference (or pupil signal difference), is a function of the pitch walking deviation, from the target value of delta $\Delta$. On the other hand, the average spectrum of these two gratings is less sensitive to the deviation of the pitch walking from the target value.

The test structure including gratings pair configured as described above is to make both gratings compatible to the design rule. Preferably, the pair of gratings is placed as close as possible to one another to provide that all geometrical parameters on the printed profiles on both gratings are similar, with the exception of designed difference in mandrel CDs and/or period. At least some and preferably all underneath layers, if any, in the test site are the same for the gratings pair.

Optimization of the target dimensions can be done if allowed by design rules. One of the parameters that need to be defined is the deviation, $\Delta$, from the target. The value of $\Delta$ is actually defined by the expected process window (or range) of pitch walking, and is preferably larger or equal to the pitch walking range. In cases when the expected pitch walking range is too large to allow the use of the target period, a larger period can be used in the gratings of the test structure, if allowed by design rules. In this case, based on the design rules restrictions, the test site optimization can be performed to define a best period and/or CD_m to ensure all grating targets are processed well in the large pitch walking process window. Using the CD (feature of the pattern, typically a width) variation and preferably also period variations allow to choose the best set of test site structures for any type of multiple patterning. Optimization can be also performed to improve spectral (pupil) sensitivity to pitch walking.

It should be noted that, in addition to the use of the test structure configured as described above, special algorithm and interpretation sequence for data processing can be used, to allow fast and accurate interpretation of measured data (based on spectral and/or pupil and/or Ellipsometry measurement and/or other existing OCD methods).

Figure 4A:
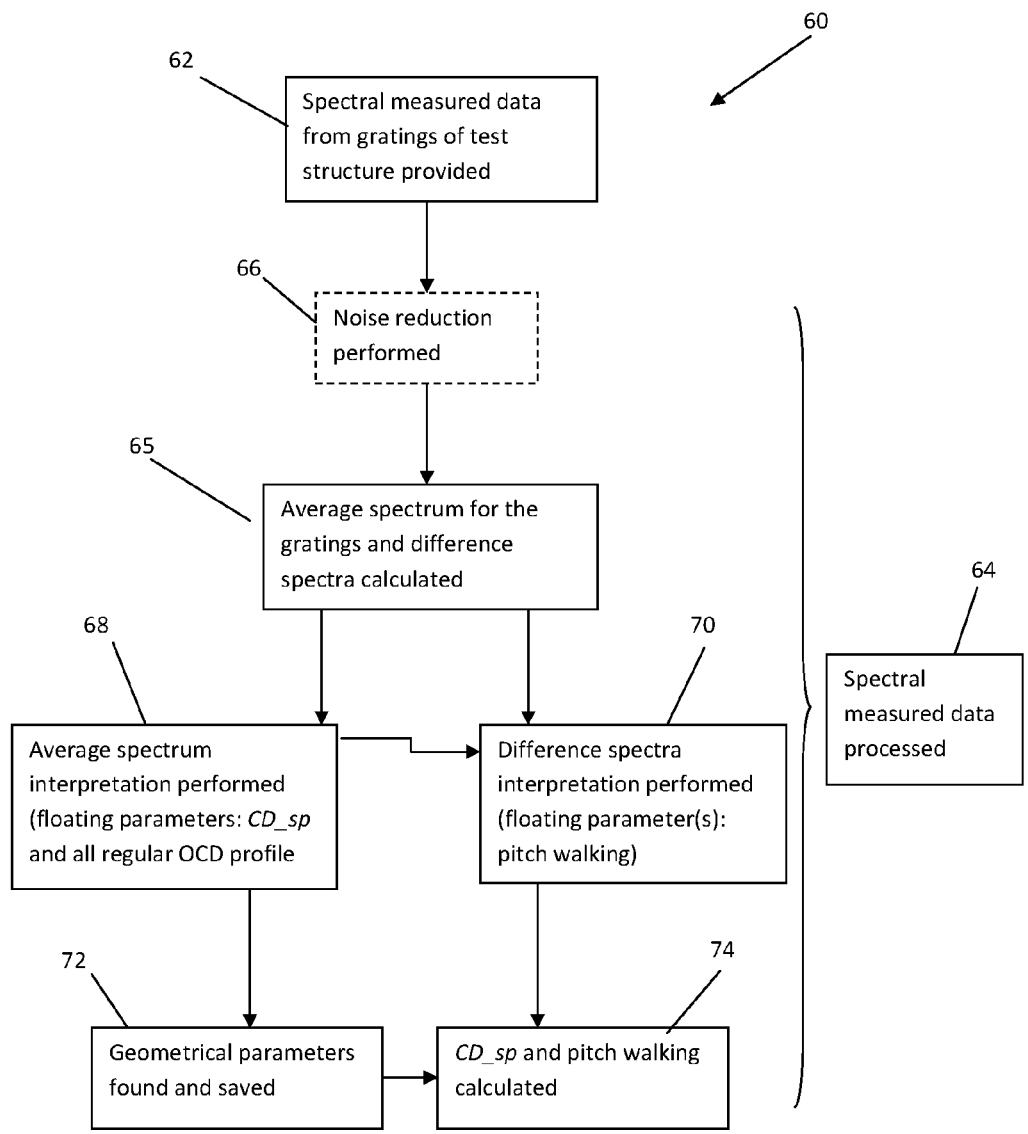
FIG. 4A shows a flow diagram of an example of a model-based method of the invention for using special algorithm and data interpretation sequence for processing and analyzing data measured on a test structure.
Figure 4B:
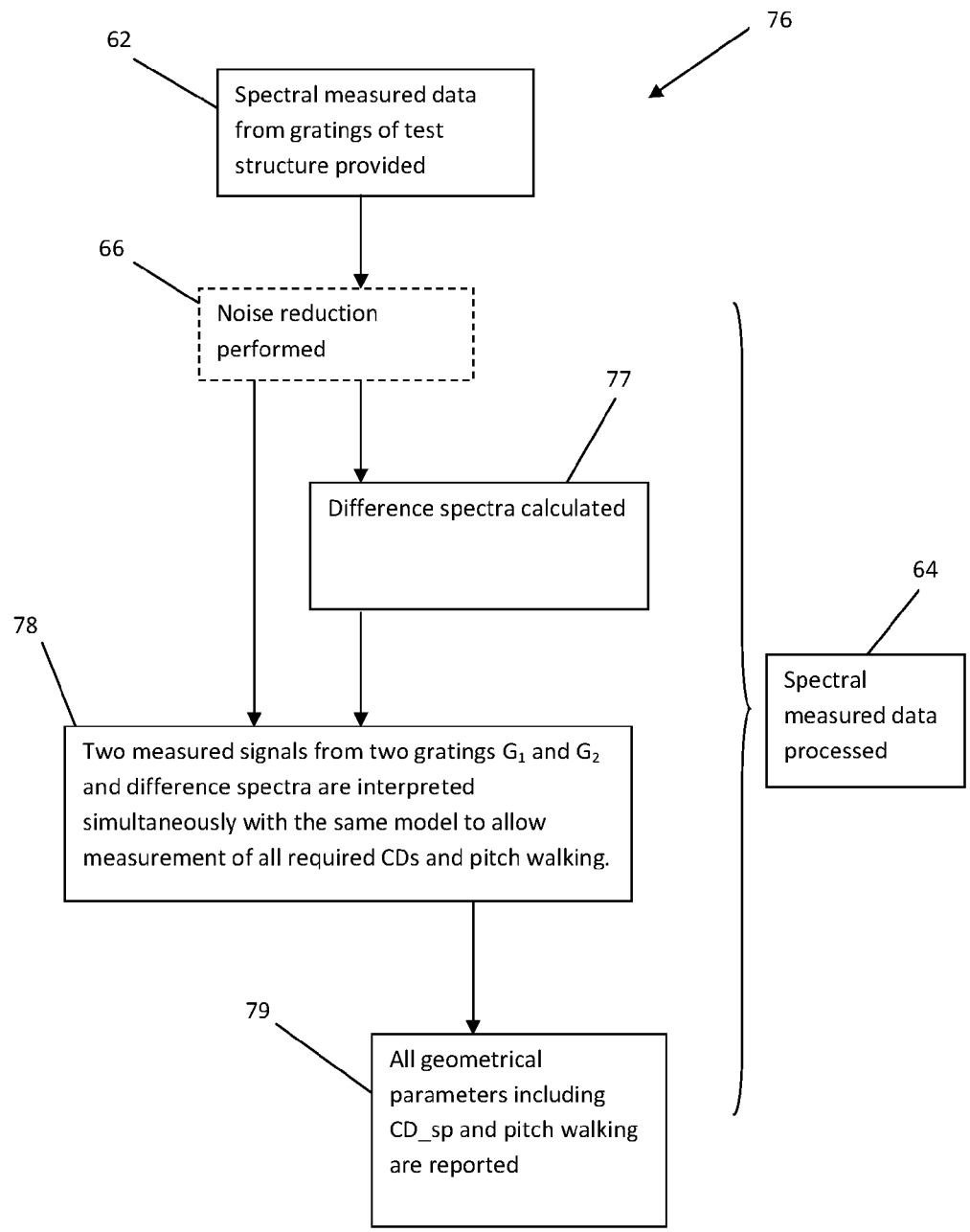
FIG. 4B shows an example of the model based data processing technique, utilizing combined simultaneous interpretation of three optical response functions.
Figure 4C:
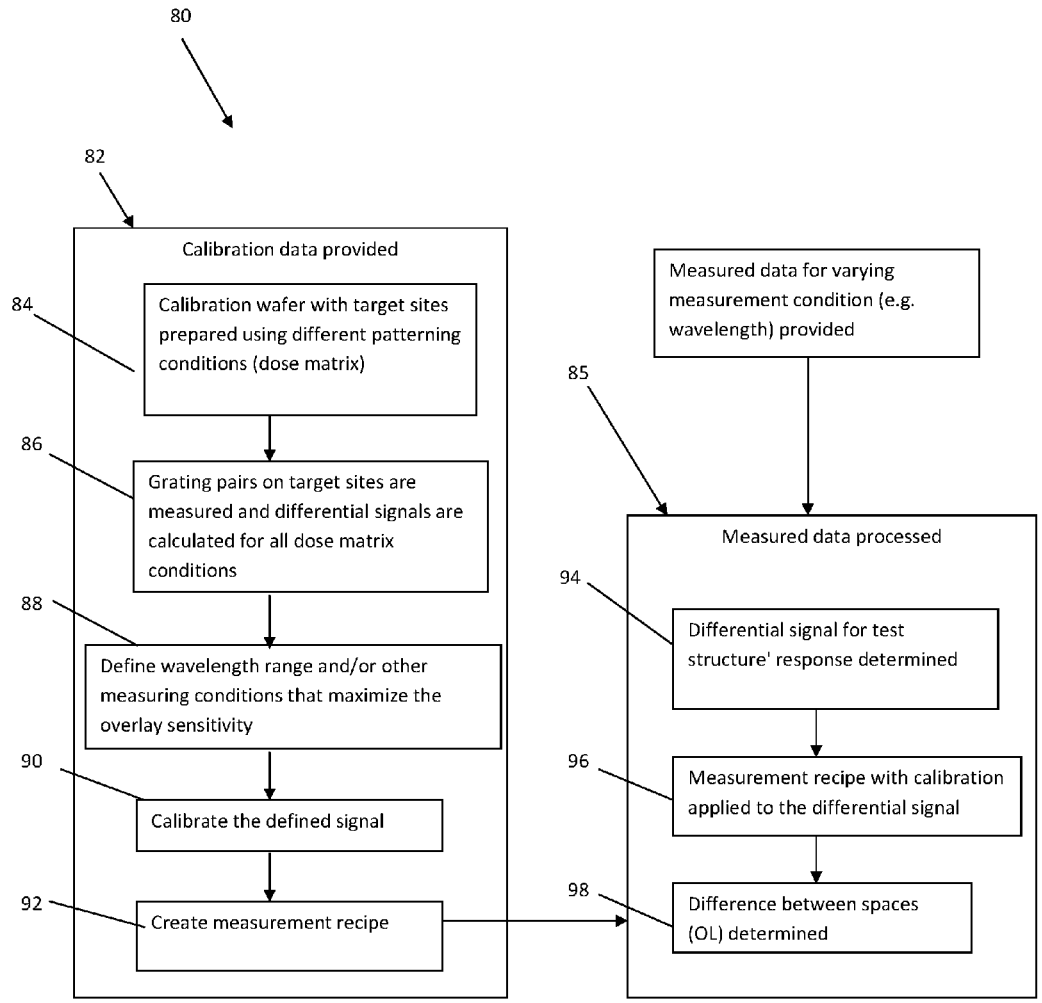
FIG. 4C shows a flow diagram of another example of a modeless method of the invention for using special algorithm and data interpretation sequence for processing and analyzing data measured on a test structure.

Reference is made to FIGS. 4A, 4B and 4C showing different examples of a method of the invention for processing and analyzing measured data (optical response) from the test structure for determining the pitch walking effect induced by the multiple patterning process, and thus enabling to control the process. In the example of FIG. 4A, the data processing method is a model based method, i.e. utilizes measured data interpretation based on a predetermined model describing optical response (theoretical data) from a similar structure under similar measurement conditions. FIG. 4B shows a somewhat different example of the model based data processing technique, utilizing combined simultaneous interpretation of three optical response functions (based on the example of a pair of gratings). In the example of FIG. 4C, the data processing is modeless, utilizing predetermined calibration data.

FIG. 4A exemplifies a flow diagram 60 of the data processing method of the invention using special algorithm and data interpretation sequence. According to this method, spectral measured data (or "pupil" or "angular" response indicative of signal distribution in pupil plane) from a test structure including a pair of gratings arranged as described above is provided (step 62). This spectral measured data is received from a measurement system or is accessed from a storage device (as the case may be). The spectral measured data is processed (step 64). The processing includes calculation of average spectrum (pupil signal) and difference spectrum (pupil signal)—step 65. Optionally, noise reduction processing can be applied (step 66). The average spectrum is calculated as reflectance from the two gratings of the test structure averaged per wavelength (or per pupil angle). The difference spectrum is calculated as a difference per wavelength (or per pupil angle) in the reflectance signal from the two gratings. Interpretation of the average spectra (average pupil signal) is then performed (step 68) with the target pitch walking equal to $\Delta$. The floating parameters include: CD_sp and all regular OCD profile parameters, while two space CDs are maintained different by $\Delta$ (spaces are defined as $((P-2CD\_Sp)/2+\frac{1}{2}\Delta)$ and $((P-2CD\_Sp)/2-\frac{1}{2}\Delta)$. In this case, interpretation of average spectra is similar to the standard OCD application. Geometrical parameters found by the interpretation of the average spectra (or average pupil signal), including CD_sp, are saved (step 70) to be used (e.g. by injection) at the following step. For double patterning case example, interpretation of the difference spectra (or difference pupil signal) is performed (step 72) with only one floating parameter—pitch walking. The interpretation can be performed on selected spectral regions (i.e. parts of the spectrum or signal) with maximal sensitivity to the target parameter (where other parameters are used based on interpretation from the previous step). As indicated above, a number of gratings in the test structure may or may not be equal to the number of patterning steps of the multiple patterning process to be controlled, thus, for triple and quadruple patterning, interpretation of the difference spectra (or difference pupil signal) may be performed (step 72) with more than one floating parameter. Based on the interpretation results of the average and difference spectra (or pupil signal), CD_sp and pitch walking, all CDs can be easily calculated (step 74).

According to another example, illustrated by a flow diagram 76 of FIG. 4B, of the processing and analyzing the measured data, combined simultaneous interpretation of three spectra (or pupil signals) may be performed (based on the example of a pair of gratings). Thus, similar to the above described example of FIG. 4A, optical response data (spectral data or pupil/angular response) from a test structure including a pair of gratings arranged as described above is provided (step 62), being received from a measurement system or accessed from a storage device, and is processed (step 64). The processing optionally includes noise reduction (step 66). The measured data includes two measured signals from two gratings $G_1$ and $G_2$ and adding difference spectra (or difference pupil signal). The measured data is processed to calculate a difference between the two responses (reflections) per wavelength (or per pupil angle)—step 77, and then combined interpretation is performed (step 78), namely two measured signals from two gratings $G_1$ and $G_2$ and the difference function (e.g. spectra) are interpreted simultaneously with the same model to allow measurement and reporting of all required CDs and pitch walking (step 79). Also, this combined interpretation can be performed on selected spectral (or pupil) areas with maximal sensitivity to the target parameter.

FIG. 4B shows a flow diagram 80 for the modeless method of processing the measured data. According to this example, calibration data is first prepared (step 82) and then used for processing real measured data (step 85).

The preparation of the calibration data includes preparation of a calibration wafer with target sites using different patterning conditions (dose matrix)—step 84. This may for example include variation of doze: a dose matrix is prepared at Mandrel Litho, and a set of fields are printed on a sample (wafer) each being printed with different dose settings. This allows to create a set of grating pairs (e.g. double patterning example), that have different spaces (OL) due to variations of the Mandrel CD. CD differences are usually known or can be measured by any metrology tool. Optical measurements are then applied to the grating pairs on target sites (with varying measurement condition (e.g. wavelength) and differential signals are calculated for all dose matrix conditions (step 86). The calculated differential signals provide a set of differential signals from all target pairs produced with different dose (variations of Mandrel CD), i.e. a set of differential optical response functions (e.g. spectra, considering that the varying measurement condition(s) include wavelength variation). A range for the corresponding variation of measuring condition (e.g. wavelength range) is defined (step 88), as well as that of the variation of one or more additional measuring condition(s), that maximize the overlay sensitivity. Noise reduction, averaging, and other signal processing may be applied if required. The defined signal is calibrated (step 90) with the known CD variations (that can be measured by any metrology, or utilize known dose dependence), and measurement recipe is created (step 92). Any methods (NN and similar) can be also used. It should be noted that the calibration of the defined signal can be done after noise reduction, averaging, and other signal processing.

Real measured data, i.e. measurement on real (production) samples is provided, and is analyzed utilizing the calibration data (step 85). To this end, the differential signal of the real measured data is determined (step 94), and measurement recipe with calibration is applied to the differential signal (step 96), and differences between the spaces (OL) are measured (step 98). The processing of the real measurements thus does not require prior knowledge of CDs and other structure parameters, and does not require use of any predefined model.

The following is an example illustrating the use of the technique of the present invention for FIN pitch walking (2D Si FIN grating on Oxide—SOI) measured with two measurement modes: Normal Incidence (NI) and Oblique spectral reflectometer. The grating dimensions and measurement steps are summarized in Table 2 below for the specific example of Litho (Mandrel) with CD_m=20 nm (after trim, if required) printed with immersion 193 nm lithography providing the pattern period of 80 nm. Here, Δ is the build-in mismatch between two gratings in the patterning mask set to 10 nm. Process related pitch walking was modeled to be in the range of 1 to 5 nm, due to spacer error (X) and due to Litho error (Y).

TABLE 2

| | Period | CD Mandrel (target), nm | Spacer (target), nm | Spacer error X, nm | Litho error Y, nm |
|---|---|---|---|---|---|
| Nominal | 80 | 20 | 20 | zero | zero |
| Grating 1 | 80 | 25 | 20 | +/−0.5; 1; 1.5; 2; 2.5 | +/−0.5; 1; 1.5; 2; 2.5 |
| Grating 2 | 80 | 15 | 20 | | |

Figure 5A:
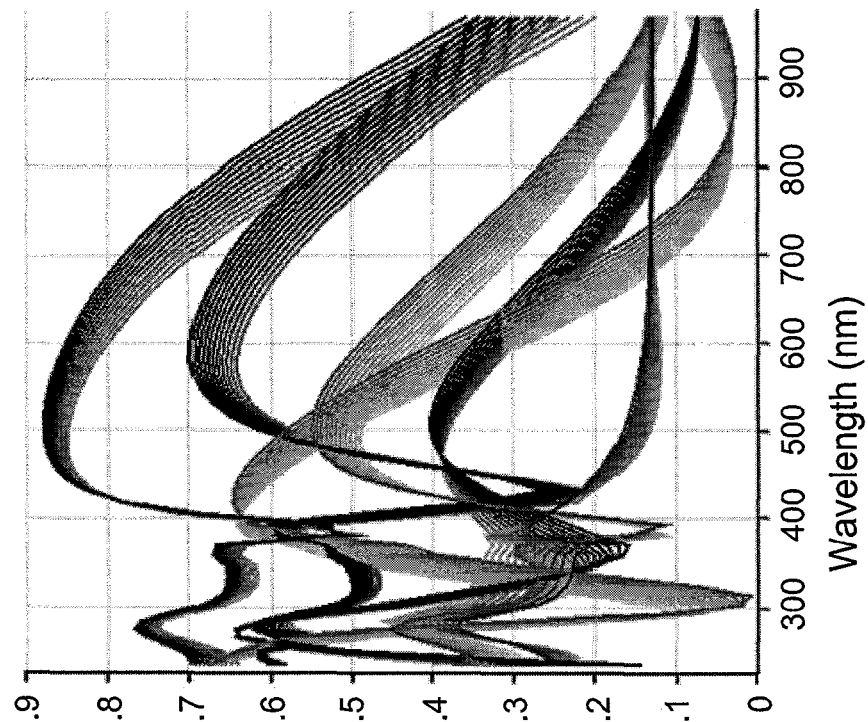
FIGS. 5A and 5B exemplify the technique of the present invention for the sensitivity of OCD spectra to Litho (Mandrel) errors and spacer errors.
Figure 5B:
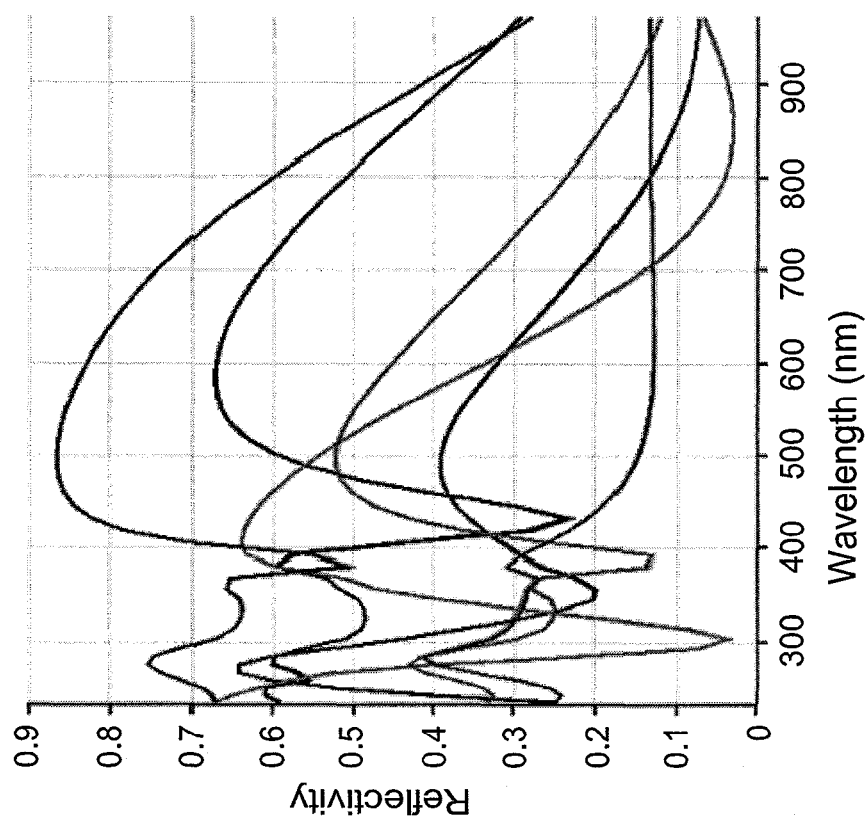

FIGS. 5A and 5B show the sensitivity of OCD spectra to Litho (Mandrel) errors and spacer errors: FIG. 5A shows spectral sensitivity to pitch walking due Litho (Mandrel) error Y (left), and FIG. 5B shows Spectral sensitivity to pitch walking due to spacer error X. In both cases, pitch walking changes are from −5 nm to +5 nm with 1 nm step. Six spectra are presented for normal incidence and oblique incidence spectra with two azimuths (0 degrees and 90 degrees), each with two polarizations. In is clearly seen that spectral sensitivity to spacer variations (FIG. 5B) is high, while sensitivity to Litho (Mandrel) variations (FIG. 5A) is extremely small Hence, it may be difficult to measure Litho component of pitch walking (Y) based on single measurement.

Figure 6A:
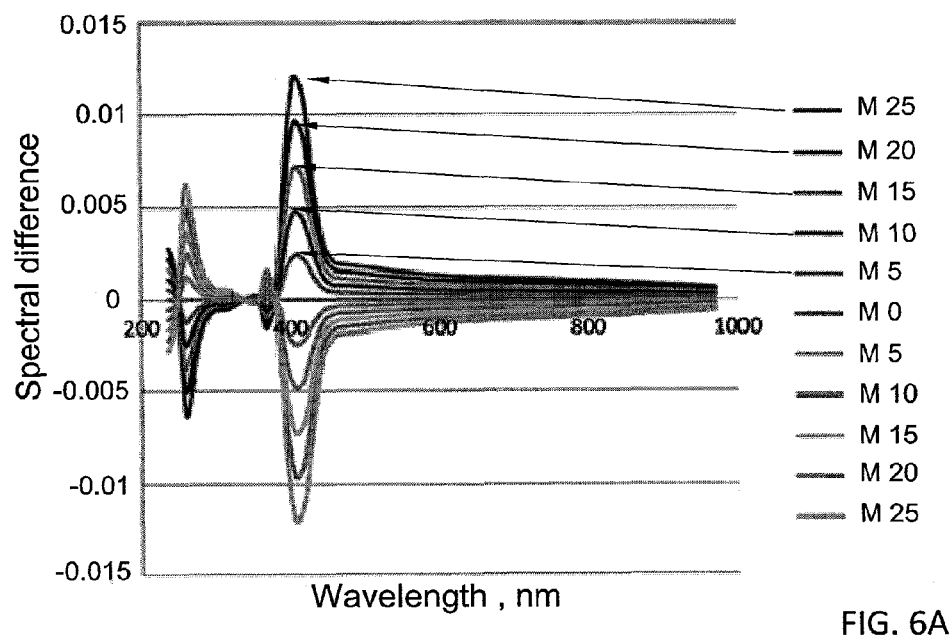
FIGS. 6A and 6B exemplify the technique of the present invention, where
Figure 6B:
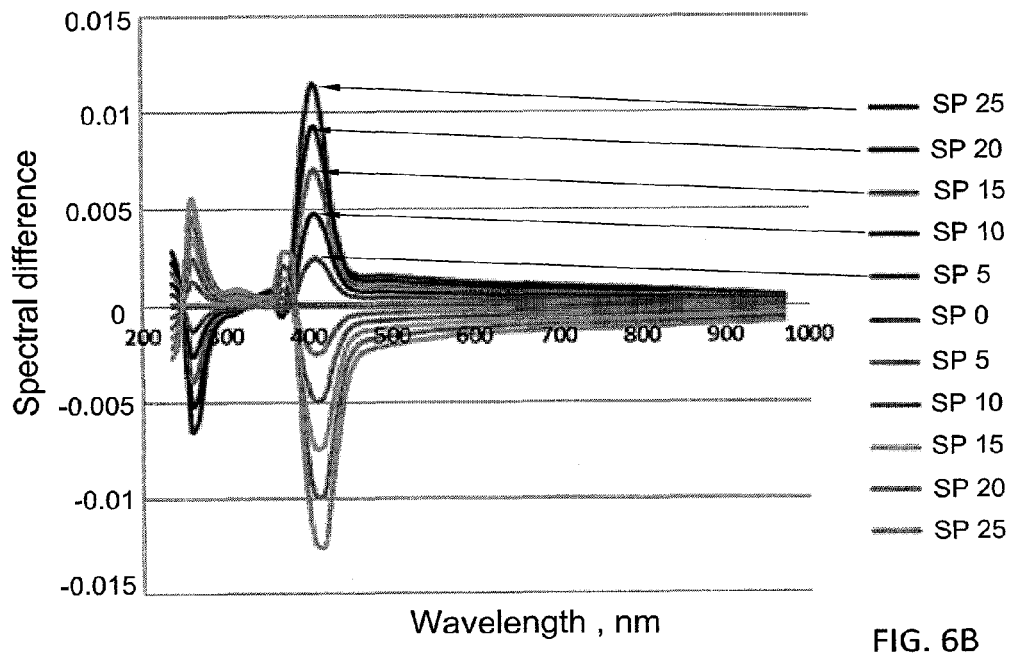

FIGS. 6A and 6B show difference spectra (spectral sensitivity to pitch walking) for Mandrel error (FIG. 6A) and for spacer error (FIG. 6B. In both cases, pitch walking changes are from −5 nm to +5 nm with 1 nm step. Six spectra are presented for normal, oblique with azimuth 0 degrees and oblique with azimuth 90 degrees. For simplicity, only normal incidence TE spectral differences are shown. As expected, differential signals are similar in both cases, and difference is defined mainly by pitch walking.

It should be noted that large spectral variations due to different spacer CDs (spacer errors) almost completely disappear in the case of differential spectra. Clear spectral signature of Difference spectra show that best sensitivity spectral areas can be chosen for interpretation to allow usage of spectral enhancements and noise reduction techniques to measure even minor pitch walking errors. These best sensitivity spectral areas are chosen in each of spectral (or pupil signal) components, including but not limited to: polarization/angle of incidence/azimuth, etc., based on the sensitivity analysis, as in the current example, or based on measured spectral response.

Alternatively, or additionally to the data processing method described above, special data processing can be used to allow modeless measurements (i.e. without the need for interpretation) of pitch walking, based on calibration.

Clear spectral signature of difference spectra (FIGS. 6A and 6B) that is independent of large variations of other strong profile parameters (such as CD_sp) allows for using calibration techniques to measure overlay error (OL) without complex modeling, in a fast and reliable way. In the current example, average and/or integral differential signal in spectral areas of 250-350 nm and/or 400-450 nm is proportional to X and Y components of pitch walking. So, as in the model based approach, good choice of best sensitivity areas, together with usage of spectral enhancements and noise reduction techniques allows reliable modeless measurements of the overall pitch walking. It should be noted that the example described herein is simplified, and much more complex indications or mathematical functions on the spectra can be used as a basis for such modeless solution.

This option (modeless data analysis, based on calibration) can be beneficial for the cases when modeling is problematic, such as multiple patterning over complex structures located below. Modeless option can also enable in-die measurements, where it is difficult or impossible to model and account for all parameters' variations (especially for under laying structures).

Calibration of the modeless approach can be done on the simple Focus Exposure Matrix (FEM) wafer or even Dose Matrix (DM) wafer processed through multiple patterning sequence. In this case, both the magnitude of pitch walking and the areas of best spectral sensitivity can be easily found to allow calibration of the Difference spectra.

Thus, the present invention provides a simple and effective technique for accurate controlling of multiple patterning techniques, operable with any existing scatterometry measurement system. The invention is thus neither limited to any OCD measurement techniques, as well as any specific multiple patterning techniques, such as SADP for example.

The invention claimed is:

1. A method for use in controlling a multiple patterning process applied to a sample to produce a target pattern thereon, the method comprising:

providing a test structure within a test site on the sample, wherein said test structure is configured for controlling the multiple patterning process to produce the target pattern, and comprises at least one pair of gratings, first and second gratings of the pair being in the form of first and second patterns of alternating features and spaces and differ from the target pattern by different first and second values which are selected to provide together a total difference such that a differential optical response from said test structure is indicative of a pitch walking effect expected in the multiple patterning process which is to be controlled; said providing of the test structure comprises:

applying a mandrel mask to an article to create a first, core pattern thereon, said mandrel mask comprising a mandrel layout defining a test site carrying a test structure, thereby creating a corresponding test structure within a test site on the article, while forming the mandrel pattern thereon, wherein said test structure in the mandrel comprises at least first and second gratings having first and second patterns with first and second critical dimension different from a critical dimension of the mandrel layout by predetermined first and second values selected in accordance with expected pitch walking effect characterizing the multiple patterning process;

applying optical measurements to the test structure and detecting optical responses of the gratings in the test structure; and processing and analyzing data indicative of the detected optical responses to determine the differential optical response and identify the pitch walking effect.

2. The method according to claim 1, wherein said total difference value is selected to be proportional to a predefined value corresponding to the process window of the pitch walking effect.

3. The method according to claim 2, wherein proportion factors for the different gratings is selected such that the total difference is substantially equal to the pitch walking effect.

4. The method according to claim 1, wherein the test structure comprises at least one additional pair of gratings.

5. The method according to claim 1, wherein a number of the gratings in the test structure is equal to a number of patterning steps in the multiple patterning process.

6. The method according to claim 1, wherein a number of the gratings in the test structure is smaller than a number of patterning steps in the multiple patterning process.

7. The method according to claim 1, wherein the test structure is configured for controlling double patterning process.

8. The method according to claim 1, wherein differential optical response from the test structure indicative of a pitch walking effect is measured as a function of at least one varying measuring condition.

9. The method according to claim 8, wherein the at least one different measurement condition comprises at least one of the following: different wavelengths of illumination, different polarizations, different angles of light collection.

10. The method according to claim 1, wherein said sample is a semiconductor wafer prepared to undergo said multiple patterning process to be controlled for producing the target pattern on the sample.

11. The method according to claim 10, wherein the test site is located within a scribe line or in-die region of the wafer.

12. The method according to claim 1, wherein said optical measurements comprise measurements with different measurement conditions, such that the optical response is in the form of detected light as a function of said measurement condition.

13. The method according to claim 12, wherein the different measurement conditions comprise at least one of the following: different wavelengths of illumination, different polarizations, different angles of light collection.

14. The method according to claim 13, wherein said processing and analyzing of the data indicative of the optical responses is based on a predetermined model.

15. The method according to claim 14, wherein processing and analyzing of the data indicative of the optical responses comprises: determining the differential optical response function between the first and second gratings.

16. The method according to claim 15, wherein the determination of the differential optical response function comprises processing averaged optical response functions for the first and second gratings.

17. The method according to claim 16, wherein said processing comprises interpreting the average and the differential functions using a predetermined model, and determining at least the pitch walking effect.

18. The method according to claim 15, wherein said processing comprises simultaneously interpreting the differential function and the optical responses of the first and second gratings, using a predetermined model, and determining at least the pitch walking effect.

19. The method according to claim 13, wherein said processing and analyzing of the data indicative of the optical response functions comprises: determining a difference of the optical response function between the first and second gratings; and analyzing said difference utilizing predetermined calibration data, to thereby obtain data indicative of the pitch walking effect.

20. The method according to claim 1, wherein said multiple patterning process is a spacer self-aligned multiple patterning.

21. The method according to claim 20, wherein said multiple patterning process is a spacer self-aligned double patterning.

22. The method according to claim 21, wherein said first and second patterns of the pair of gratings in the test structure are configured for controlling the double patterning process, the first and second patterns having first and second dimensions for one of the feature and space of the pattern $(CD\_m)_1$ and $(CD\_m)_2$ satisfying a condition:

$$(CD\_m)_1 = CD\_m + (0.5 \cdot \Delta) \text{ and } (CD\_m)_2 = CD\_m - (0.5 \cdot \Delta),$$

wherein $CD\_m$ is the corresponding dimension in the target pattern; and $\Delta$ is said predefined value corresponding to the pitch walking effect characterizing said double patterning process.

* * * * *